United States Patent
Jeong (10) Patent No.: US 10,330,609 B2
(45) Date of Patent: Jun. 25, 2019

(54) METHOD AND APPARATUS OF INSPECTING A SUBSTRATE WITH A COMPONENT MOUNTED THEREON

(71) Applicant: KOH YOUNG TECHNOLOGY INC., Seoul (KR)

(72) Inventor: Joong-Ki Jeong, Gwangmyeong-si (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 0 days.

(21) Appl. No.: 15/536,213

(22) PCT Filed: Dec. 16, 2015

(86) PCT No.: PCT/KR2015/013814
§ 371 (c)(1),
(2) Date: Jun. 15, 2017

(87) PCT Pub. No.: WO2016/099154
PCT Pub. Date: Jun. 23, 2016

(65) Prior Publication Data
US 2017/0363548 A1 Dec. 21, 2017

(30) Foreign Application Priority Data
Dec. 16, 2014 (KR) ........................ 10-2014-0181723

(51) Int. Cl.
*G01N 21/88* (2006.01)
*G01N 21/956* (2006.01)
(Continued)

(52) U.S. Cl.
CPC ... *G01N 21/95607* (2013.01); *G01B 11/0608* (2013.01); *G01B 11/2513* (2013.01);
(Continued)

(58) Field of Classification Search
CPC ..... G01N 2021/9513; G01N 21/95623; G01N 2021/95638; G01N 21/9501;
(Continued)

(56) References Cited

U.S. PATENT DOCUMENTS

2004/0105093 A1* 6/2004 Hamamatsu ....... G01N 21/8806
356/237.4
2006/0174480 A1 8/2006 Kawada
2010/0290696 A1* 11/2010 Jeong ................. G01B 11/0608
382/147

FOREIGN PATENT DOCUMENTS

JP 6-347232 12/1994
JP 2004-340832 12/2004
(Continued)

OTHER PUBLICATIONS

International Search Report for International Application No: PCT/KR2015/013814, dated Feb. 25, 2016.
(Continued)

*Primary Examiner* — Michael P Stafira
(74) *Attorney, Agent, or Firm* — Kile Park Reed & Houtteman PLLC (57) ABSTRACT

A method and an apparatus of inspecting a substrate with a component mounted thereon, which are capable of inspecting whether the component is properly mounted or not without additional setting or changing inspection condition, are provided. The method comprises measuring a three-dimensional shape by irradiating the pattern image toward the substrate through at least one illumination unit and by taking a reflected image through an imaging unit, extracting a shield region from the three-dimensional shape, and inspecting a component mounting defect in an area excluding the shield region in the three-dimensional shape.

15 Claims, 5 Drawing Sheets

(51) Int. Cl.
- *H05K 13/08* (2006.01)
- *G01B 11/25* (2006.01)
- *G01B 11/06* (2006.01)
- *G06T 7/00* (2017.01)
- *G06T 7/521* (2017.01)

(52) U.S. Cl.
CPC ..... *G01B 11/2527* (2013.01); *G01N 21/8806* (2013.01); *G01N 21/956* (2013.01); *G06T 7/0004* (2013.01); *G06T 7/0006* (2013.01); *G06T 7/0008* (2013.01); *G06T 7/521* (2017.01); *H05K 13/08* (2013.01); *G01N 2021/8829* (2013.01); *G01N 2021/8835* (2013.01); *G01N 2021/8887* (2013.01); *G01N 2021/95638* (2013.01); *G01N 2201/061* (2013.01); *G06T 2207/10024* (2013.01); *G06T 2207/10028* (2013.01); *G06T 2207/30141* (2013.01)

(58) Field of Classification Search
CPC ......... G01N 21/956; G01N 2201/0638; G01N 23/2206; G01N 2021/8829; G01N 2021/8835; G01N 2021/8887; G01N 21/88; G01N 21/8803
See application file for complete search history.

(56) References Cited

FOREIGN PATENT DOCUMENTS

| | | |
|---|---|---|
| KR | 10-1992-0006031 | 7/1992 |
| KR | 10-1997-0058512 | 7/1997 |
| KR | 10-2011-0063966 | 6/2011 |
| KR | 10-2011-0088967 | 8/2011 |
| KR | 10-2013-0098221 | 9/2013 |
| KR | 10-2013-0107547 | 10/2013 |

OTHER PUBLICATIONS

Supplementary European Search Report for European Patent Application No. 15870321.5, dated Jun. 18, 2018.

* cited by examiner

METHOD AND APPARATUS OF INSPECTING A SUBSTRATE WITH A COMPONENT MOUNTED THEREON

TECHNICAL FIELD

The present invention relates to a method and an apparatus of inspecting a substrate with a component mounted thereon, and more particularly, the present invention relates to a method and an apparatus of inspecting a substrate with a shield together with a component.

BACKGROUND ART

Generally, at least one printed circuit board (PCB) is provided in an electronic device, and the PCB includes a component such as a chip. An operation of inspecting a component such as the chip on the PCB is necessary to determine whether the component mounted on the PCB is defective or to judge whether a pad connected to the component is defective.

For detecting the defectiveness, a three-dimensional shape measuring apparatus using a grid pattern can be used. That is, by measuring the three-dimensional shape, it is checked whether the component is misaligned, whether the component is not mounted, whether the solder is over-coated, or not-coated.

Figure 1:
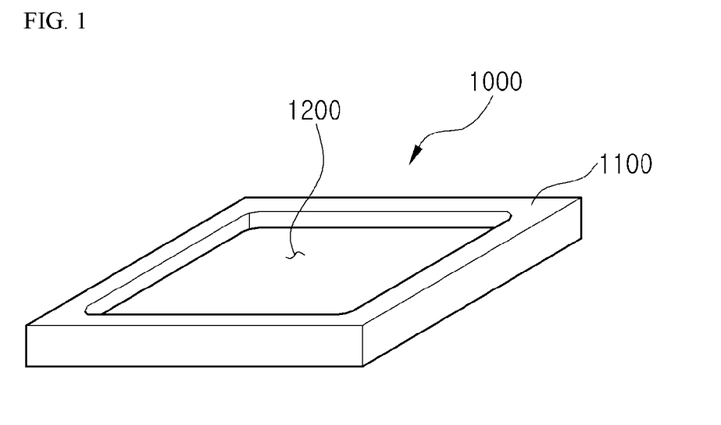
FIG. 1 is a perspective view illustrating a shield for eliminating mutual interference between functional blocks in a substrate.

On the other hand, electronic devices such as smart phones have various functions. That is, in addition to basic communication functions, electronic devices such as a smart phone have additional functions for taking charge of a camera, a DMB, and a GPS function, etc. In manufacturing the electronic devices with multiple functions, components for performing same function are mounted being concentrated in space to form a functional block, and a shield 1000 is attached so as to surround the functional blocks respectively in order to eliminate electrical interference between the functional blocks as shown in FIG. 1.

However, there is a case where the mounting state of the component is hid by the edge portion 1100 of the shield 1000 for improving the electromagnetic wave shielding function. In the case of components mounted in region corresponding to the opening 1200 of the shield 1000, there is no problem to check the mounting state of the components. However, component covered by the edge portion 1100 of the shield 1000 cannot be inspected.

However, there is an inspection request even for the remaining portions other than the covered portion, and inspection is performed by differently setting each component, since an amount and a shape of covered portions of components covered by the edge portion 1100 of the shield 1000 are different from each other in order to inspect the remaining portions of the component.

Figure 2A:
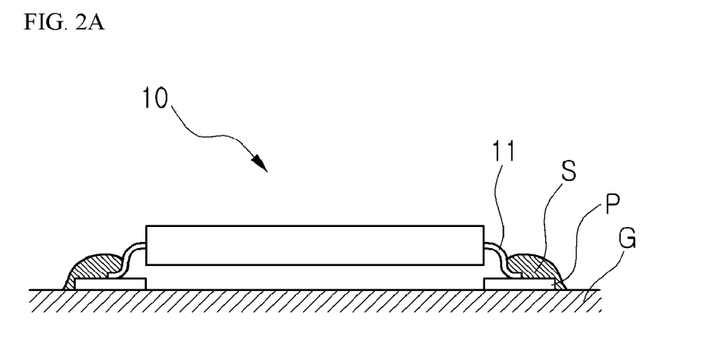
FIG. 2A is a cross-sectional view showing a mounted state of a component not covered by a shield.
Figure 2B:
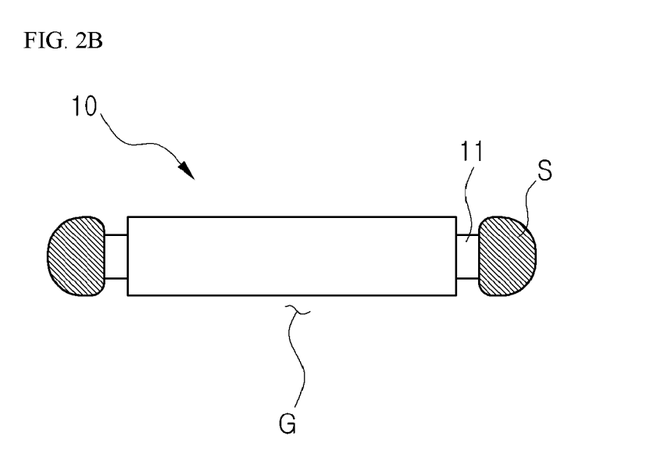
FIG. 2B is a plan view showing the mounting state of the component shown in FIG. 2A.
Figure 3A:
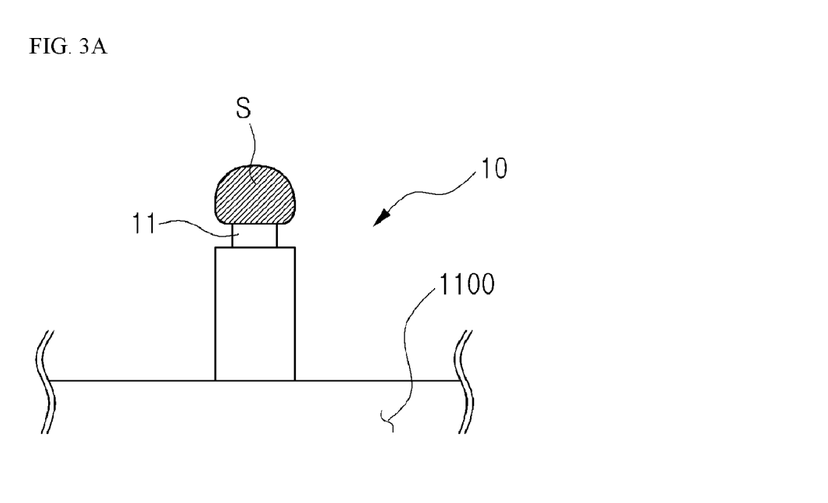
FIGS. 3A and 3B are plan views showing components mounted differently in a covering state by a shield.
Figure 3B:
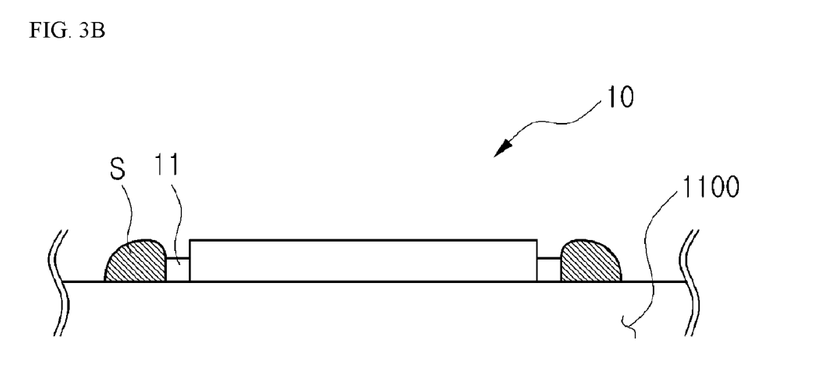

That is, as shown in FIGS. 2A and 2B, the lead 11 of the component 10, which is a measurement object, is attached to the pad P formed on the substrate G by using the solder paste S. In the case of inspecting the components 10 mounted differently from each other in a state of being shielded by the edge portion 1100 of the shield 1000 as shown in FIGS. 3A and 3B, it takes a lot of time to inspect the components 10 by changing the setting for each case in judging the components 10 if the components are properly mounted.

DETAILED DESCRIPTION OF THE INVENTION

Objects of the Invention

Accordingly, it is an object of the present invention to provide a method and an apparatus of inspecting a substrate with a component mounted thereon, which is capable of judging a mounting state of the component through a common setting without changing the setting or inspection conditions, even when the component is covered by an edge portion of a shield.

Technical Solution

In order to solve the problems described above, a method of inspecting a substrate with a component mounted thereon, according to an exemplary embodiment of the present invention, comprises measuring a three-dimensional shape by irradiating the pattern image toward the substrate through at least one illumination unit and by taking a reflected image through an imaging unit, extracting a shield region from the three-dimensional shape, and inspecting a component mounting defect in an area excluding the shield region in the three-dimensional shape.

In this case, extracting the shield region from the three-dimensional shape may be performed by determining a region higher than a height of the component as the shield region.

Further, inspecting a component mounting defect in an area excluding the shield region in the three-dimensional shape, may be performed by applying an inspection condition, which is previously set, to the component under the shield region, after the component under the shied region is recognized by using at least one of CAD information and component library information.

In order to solve the problems described above, a method of inspecting a substrate with a component mounted thereon, according to another exemplary embodiment of the present invention, comprises obtaining two-dimensional image through an image capturing unit, extracting a shield region by using the two-dimensional image, and inspecting a component mounting defect in an area excluding the shield region.

In this case, extracting a shield region by using the two-dimensional image may be performed by extracting the shield region by using at least one of brightness and color in the two-dimensional image.

For example, the method may further comprise measuring a three-dimensional shape by irradiating the pattern image toward the substrate through at least one illumination unit and by taking a reflected image through an imaging unit, before obtaining two-dimensional image through an image capturing unit. In this case, the shield region is extracted in the three-dimensional shape.

Further, extracting a shield region by using the two-dimensional image may be performed by further using the three-dimensional shape.

Further, extracting a shield region by using the two-dimensional image and the three-dimensional shape may be performed by determining a region higher than a height of the component as the shield region.

Further, inspecting a component mounting defect in an area excluding the shield region, may be performed by applying an inspection condition, which is previously set, to the component under the shield region, after the component under the shied region is recognized by using at least one of CAD information and component library information.

An apparatus of inspecting a substrate with a component mounted thereon, according to an exemplary embodiment of the present invention comprises an image capturing unit and a central control unit. The image capturing unit captures an image reflected from a measurement object. The central control unit extracts a shield region from the image and inspects a defect of a component in an area excluding the shield region.

For example, the central control unit may determine a region higher than a height of the component as the shield region.

Further, the central control unit may apply an inspection condition, which is previously set, to the component under the shield region, after the shied region is recognized by using at least one of CAD information and component library information.

Alternatively, the image capturing unit may capture a two-dimensional image, and the central control unit may determine the shield region using at least one of brightness and color of the two-dimensional image.

Further, the central control unit may apply an inspection condition, which is previously set, to the component under the shied region, after recognizing the component under the shield region by using at least one of CAD information and component library information in order to inspect the component mounting failure in the area excluding the shield region.

The apparatus may further comprise an illumination unit irradiating a pattern to the measurement object. In this case, the image may comprise a pattern image by the pattern, and the central control unit may obtain a three-dimensional shape from the pattern image, and may extract the shield region from the three-dimensional shape.

An apparatus supporting a component mounting defect inspection of a substrate with a shield mounted thereon, according to an exemplary embodiment of the present invention provides an interface for displaying an image obtained by an image capturing unit, provides an interface for extracting a shield region by using the image, and provides an interface for inspecting a component mounting defect in an area excluding the shield region.

Advantageous Effects

According to the method and the apparatus of inspecting a substrate with a component mounted thereon according to the present invention, it is possible to judge whether the components are mounted properly or not, through the common setting without changing the setting or inspection condition, so that the inspection speed can be improved, even if the components are covered by an edge portion of a shield.

MODE FOR INVENTION

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art.

It will be understood that, although the terms first, second, third etc. may be used herein to describe various elements, components, regions, layers and/or sections, these elements, components, and/or sections should not be limited by these terms. These terms are only used to distinguish one element, component, region, layer or section from another region, layer or section. Thus, a first element, component, or section discussed below could be termed a second element, component, or section without departing from the teachings of the present invention.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs.

It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, preferred embodiments of the present invention will be described in detail with reference to the drawings.

Figure 4:
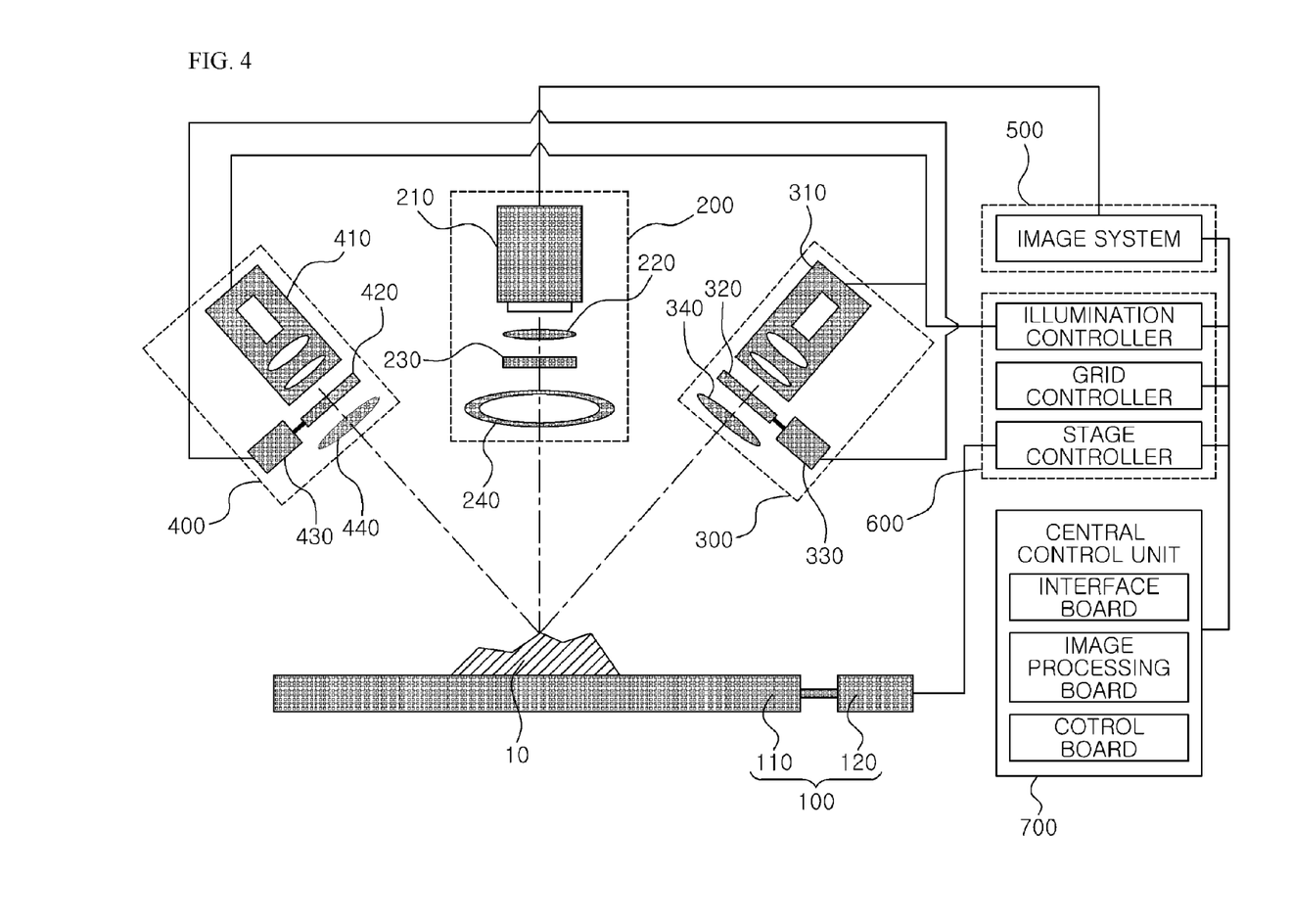
FIG. 4 is a conceptual diagram showing a three-dimensional shape measuring apparatus used in a three-dimensional shape measuring method according to an exemplary embodiment of the present invention.

FIG. 4 is a conceptual diagram showing a three-dimensional shape measuring apparatus used in a three-dimensional shape measuring method according to an exemplary embodiment of the present invention.

Referring to FIG. 4, a three-dimensional shape measuring apparatus used in the three-dimensional shape measuring method according to the present exemplary embodiment, may include a measurement stage unit 100, an image capturing unit 200, first and second illumination units 300 and 400, an image acquisition unit 500, a module control unit 600, and a central control unit 700.

The measurement stage unit 100 may include a stage 110 for supporting a measurement object 10 and a stage transfer unit 120 for transferring the stage 110. In this embodiment, as the measurement object 10 is moved by the stage 110 relative to the image capturing unit 200 and the first and second illumination units 300 and 400, the measurement position of measurement can be changed.

The image capturing unit 200 is disposed over the stage 110 and receives light reflected from the measurement object 10 to measure an image of the measurement object 10. That is, the image capturing unit 200 receives the light emitted from the first and second illumination units 300 and 400 and reflected by the measurement object 10, and captures a plane image of the measurement object 10.

The image capturing unit 200 may include a camera 210, an image forming lens 220, a filter 230 and a lamp 240. The camera 210 receives the light reflected from the measurement object 10 and takes a plane image of the measurement object 10. For example, any one of a CCD camera and a CMOS camera may be employed. The image forming lens 220 is disposed below the camera 210 to image the light reflected from the measurement object 10 at the camera 210. The filter 230 is disposed below the image forming lens 220 to filter light reflected by the measurement object 10 and to provide the image to the image forming lens 220. For example, the filter 230 may include one of frequency filter, a color filter and an intensity adjustment filter. For example, the lamp 240 may be circularly arranged under the filter 230, or may be disposed separately from the image capturing unit 200, and may be composed of a plurality of LEDs. In addition, the lamp 240 may provide light to the measurement object 10 in order to capture a specific image such as a two-dimensional shape of the measurement object 10.

The image capturing unit 200 may be disposed in a direction perpendicular to a plane or may be inclined with respect to a normal perpendicular to a plane. When the image capturing unit 200 includes a plurality of image capturing units, at least one image capturing unit may be disposed in a direction perpendicular to a plane or may be inclined with respect to a normal perpendicular to a plane. Of course, when a mirror or a beam splitter is employed between the measurement object 10 and the image capturing unit 200, the image capturing unit 200 may be disposed in parallel with the plane.

The image capturing unit 200 may perform at least of capturing an image of light irradiated from the lamp 240 and reflected by the measurement object 10, and capturing a grid-patterned light irradiated from the first and second illumination units 300 and 400 and reflected by the measurement object 10.

The first illumination unit 300 may be disposed such that the first illumination unit 300 irradiates the measurement object 10 in a direction perpendicular to the plane of the measurement object 10 or in a direction inclined with respect to the stage 110 supporting the measurement object 10 in a right side of the image capture unit 200. The first illumination unit 300 may include a first illumination unit 310, a first grating unit 320, a first grating transfer unit 330 and a first condensing lens 340. The first illumination unit 310 includes an illumination source and at least one lens to generate light. The first grating unit 320 is disposed below the first illumination unit 310, and transforms the light generated by the first illumination unit 310 to the first grid-patterned light having the grid pattern. The first grating transfer unit 330 is connected to the first grating unit 320 to transfer the first grating unit 320. For example, the first grating transfer unit 330 may be a PZT (Piezoelectric) transfer unit or a fine linear transfer unit. The first condensing lens 340 is disposed below the first grating unit 320 to condense the first grating pattern light generated from the first grating unit 320 to the measurement object 10.

The second illumination unit 400 may be disposed such that the second illumination unit 400 irradiates the measurement object 10 in a direction inclined with respect to the stage 110 supporting the measurement object 10 in a left side of the image capture unit 200. The second illumination unit 400 may include a second illumination unit 410, a second grating unit 420, a second grating transfer unit 430 and a second condensing lens 440. Since the second illuminating unit 400 is substantially the same as the first illuminating unit 300 described above, a detailed description will be omitted.

When the first illumination unit 300 irradiates first grid-patterned light to the measurement object 10 N-times, while the first grid transmission unit 330 sequentially moves the first grid unit 320 N-times, the image capturing unit 200 may sequentially acquire N-number of first pattern images by sequentially receiving the N-number of first pattern light reflected from the measurement object 10. Additionally, when the second illumination unit 400 irradiates second grid-patterned light to the measurement object 10 N-times, while the second grid transmission unit 430 sequentially moves the second grid unit 420 N-times, the image capturing unit 200 may sequentially acquire N-number of second pattern images by sequentially receiving the N-number of second pattern light reflected from the measurement object 10. In this case, N is a natural number, for example, three or four.

On the other hand, a plurality of the first illumination units 300 and a plurality of the second illumination units 400 may installed, respectively, or only the first illumination unit 300 may be installed. The first illumination unit 300 may include a liquid crystal display device. In the present embodiment, only the first and second illumination units 300 and 400 are described as an illumination apparatus for generating the first and second grid-patterned lights, but the number of the illumination units may be three or more. That is, the grid-patterned light may be irradiated to the measurement object 10 in various directions, and various types of pattern images may be captured. For example, when three illumination units are arranged in an equilateral triangle shape around the image capturing unit 200, three grid-patterned lights can be applied to the measurement object 10 in different directions. When four illumination units are arranged in a square shape around the image capturing unit 200, four grid-patterned lights can be applied to the measurement object 10 in different directions.

The image acquisition unit 500 is electrically connected to the camera 210 of the image capturing unit 200, and acquires and stores the pattern images from the camera 210. For example, the image acquisition unit 500 includes an image system for receiving and storing the N-number of first pattern images and the N-number of second pattern images captured by the camera 210.

The module control unit 600 is electrically connected to the measurement stage unit 100, the image capturing unit 200, the first illuminating unit 300 and the second illuminating unit 400 to control them. The module control unit 600 includes, for example, an illumination controller, a grid controller, and a stage controller. The illumination controller controls the first and second illumination units 310 and 410 to generate light, respectively. The grid controller controls the first and second grating transfer units 330 and 430 to move the second grating units 320 and 420, respectively. The stage controller may control the stage transfer unit 120 to move the stage 110 in an up and down direction, and in a left and right direction.

The central control unit 700 is electrically connected to the image acquisition unit 500 and the module control unit 600 to control them. In detail, the central control unit 700 receives the N-number of first pattern images and the N-number of second pattern images from the image system of the image acquisition unit 500, and processes the received N-number of first pattern images and the N-number of second pattern images to measure the three dimensional shape of the measurement object for inspecting mounting defects of a component, based on the three dimensional shape of the measurement object. Additionally, the central control unit 700 may extract a shield region and recognize a component covered by the shield region. In addition, the central control unit 700 may control the illumination controller, the grid controller and the stage controller of the module control unit 600, respectively. The central control unit 700 may include an image processing board, a control board, and an interface board.

Hereinafter, as will be described in detail with reference to a substrate inspection method for mounting the component, the central control unit 700 may determine an area higher than the height of the component to be a shield region.

In addition, the central control unit 700 may recognize the component located at the lower end of the shield region by using at least one of the CAD information and the component library information for, and then apply predetermined inspection conditions to the recognized component.

Alternatively, the central control unit 700 may use at least one of the brightness and the color of the two-dimensional image captured by the image capturing unit to determine a shield region in the three-dimensional shape.

In order to inspect the component mounting defects in the region excluding the shield region in the three-dimensional shape, the central control unit 700 may apply inspection conditions to the component recognized by using at least one of CAD information and component library information regarding to the component.

Hereinafter, a method of inspecting a substrate with a component mounted thereon, using the above-described three-dimensional shape measuring apparatus, will be described in more detail.

Figure 5:
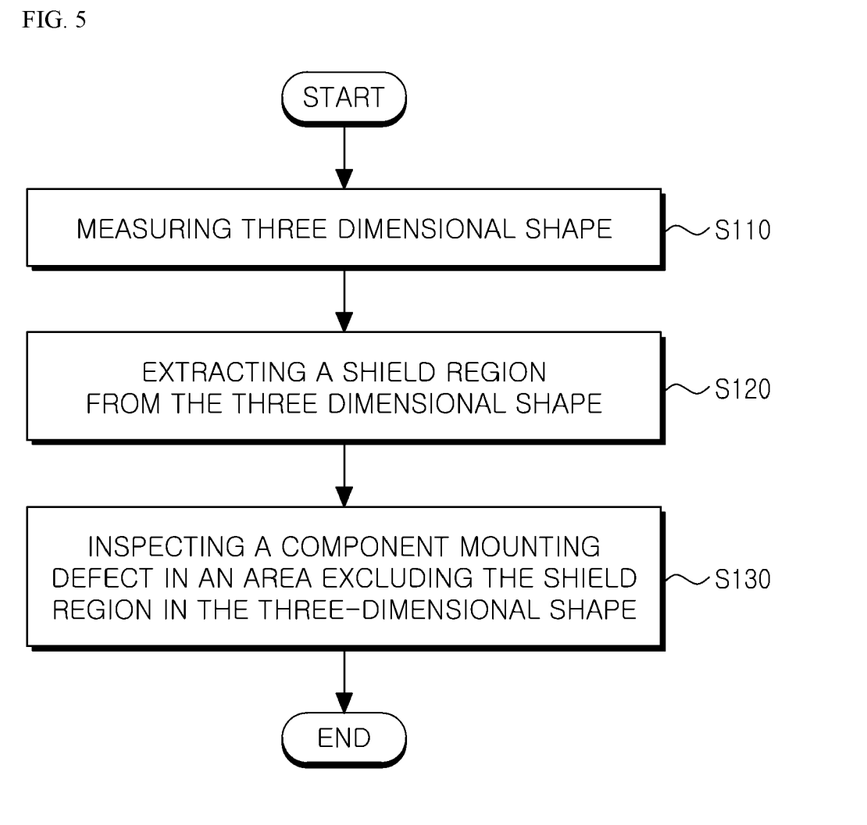
FIG. 5 is a flow chart showing a method of inspecting a substrate with a component mounted thereon.

FIG. 5 is a flow chart showing a method of inspecting a substrate with a component mounted thereon.

Referring to FIGS. 4 and 5, according to a method of inspecting a substrate with a component mounted thereon according to the present invention, a grid image is first irradiated through the at least one illumination unit 310 and 410 toward the substrate on which the measurement object 10 is mounted, the reflected image is captured through the image capturing unit 200, and the grid image is shifted and captured again to measure the three-dimensional shape (step S110).

More specifically, the image capturing unit 200 irradiates the measurement object 10 with the grid-patterned light that has passed through the grating units 320 and 420, and the outline of the three-dimensional shape of the measurement object 10 can be obtained through an optical triangulation method. That is, by measuring the height value corresponding to each position (X, Y) of the substrate, the entire outline of the substrate can be obtained.

Thereafter, the shield region is extracted from the three-dimensional shape (step S120). In order to extract such a shield region, a three-dimensional shape can be used. For example, the cross-section of the three-dimensional shape with respect to the region A in FIG. 6 can be expressed as shown in FIG. 7. In this case, a region existing at a position higher than the component 10 can be judged as a shield region.

Figure 6:
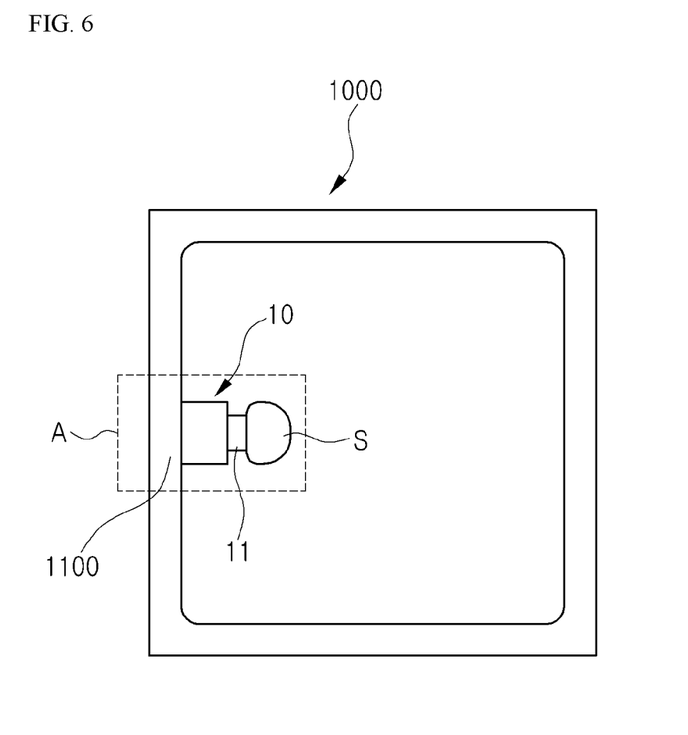
FIG. 6 is a plan view showing a two-dimensional image of a component partially covered by the shield.
Figure 7:
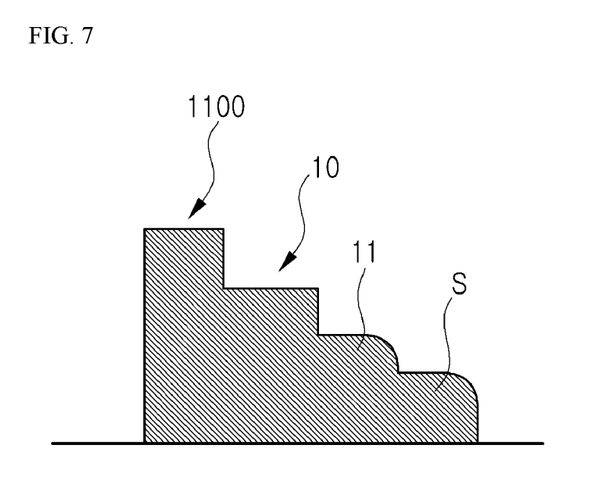
FIG. 7 is a cross-sectional view of the three-dimensional shape obtained as a result of step S110 in FIG. 5, which is a conceptual diagram showing area A in FIG. 6.

In another embodiment, in order to extract the shield region, the lamp 240 in FIG. 1 is turned on, and the coordinates (X, Y) of the edge 1100 of the shield 1000 in the two-dimensional image of FIG. 6 may be taken through the camera 210 to extract the shield region. In more detail, the shield region can be extracted using at least one of brightness and color of the shield 1000. When the shield region is extracted using the two-dimensional image in this manner, the shield region can be extracted more accurately when the height difference between the component 10 and the edge portion 1100 is not large.

In another embodiment, both the two-dimensional image and the three-dimensional shape may be considered to extract the shield region. If the brightness and color of the shield 1000 in the two-dimensional image is similar to the color and brightness of the substrate, it may not be easy to distinguish the shield 1000 from the substrate in the two-dimensional image. In this case, when the shield region is extracted in consideration of both the three-dimensional shape and the two-dimensional image, a more accurate shield region can be extracted.

Thereafter, the remaining area other than the shield region is inspected if there exists mounting defects of a component (step S130).

More specifically, when the substrate is photographed at the top, the component located under the shield region is covered by the shielding region, so that at least a portion of the component is not captured. Therefore, the portion of the component cannot be obtained in two-dimensional image or calculated in three-dimensional shape.

However, when a corresponding component is recognized to be identical with one of components with an inspection condition which is previously set, the inspection condition can be applied to the corresponding component. For this, it is possible to check the component information to be mounted at the corresponding position through the existing CAD information and to apply the inspection condition for the component. Alternatively, after the imaging of a component covered by the shield, it may be checked if the component covered by the shield is same as the existing component through the components library and the inspection condition may be reflected.

Alternatively, both of the above methods may be applied to reflect the test conditions.

Through these inspection conditions, the uncovered portion of a component may be inspected for defective mounting, such as unmount, deviation, misalignment, solder fillet, etc., based on the same inspection condition.

According to method of inspecting a substrate with a component mounted thereon, according to the present invention as described above, even if the same kind of components are shielded differently by the shield, it is possible to judge whether the component is properly mounted or not, with the common setting, so that the inspection speed can be improved.

Although the present invention has been described in the detailed description of the invention with reference to exemplary embodiments of the present invention, it will be understood to those skilled in the art that various modifications and variation can be made in the present invention without departing from the spirit or scope of the invention.

The invention claimed is:

1. A method of inspecting a substrate with a component mounted thereon, comprising:

measuring a three-dimensional shape by irradiating the pattern image toward the substrate through at least one illumination unit and by taking a reflected image through an imaging unit;

extracting a shield region from the three-dimensional shape; and inspecting a component mounting defect in an area excluding the shield region in the three-dimensional shape, wherein the shield region corresponds to such a region that at least a portion of a mounting state of the component is hid by a shield.

2. The method of claim 1, wherein extracting the shield region from the three-dimensional shape is performed by determining a region higher than a height of the component as the shield region.

3. The method of claim 1, wherein inspecting a component mounting defect in an area excluding the shield region in the three-dimensional shape, is performed by applying an inspection condition, which is previously set, to the component under the shield region, after the component under the shied region is recognized by using at least one of CAD information and component library information.

4. A method of inspecting a substrate with a component mounted thereon, comprising:

obtaining two-dimensional image through an image capturing unit;

extracting a shield region by using the two-dimensional image; and inspecting a component mounting defect in an area excluding the shield region, wherein the shield region corresponds to such a region that at least a portion of a mounting state of the component is hid by a shield.

5. The method of claim 4, wherein extracting a shield region by using the two-dimensional image is performed by extracting the shield region by using at least one of brightness and color in the two-dimensional image.

6. The method of claim 4, further comprising:

measuring a three-dimensional shape by irradiating the pattern image toward the substrate through at least one illumination unit and by taking a reflected image through an imaging unit, before obtaining two-dimensional image through an image capturing unit, and wherein the shield region is extracted in the three-dimensional shape.

7. The method of claim 6, wherein extracting a shield region by using the two-dimensional image is performed by further using the three-dimensional shape.

8. The method of claim 7, wherein extracting a shield region by using the two-dimensional image and the three-dimensional shape is performed by determining a region higher than a height of the component as the shield region.

9. The method of claim 4, wherein inspecting a component mounting defect in an area excluding the shield region, is performed by applying an inspection condition, which is previously set, to the component under the shield region, after the component under the shied region is recognized by using at least one of CAD information and component library information.

10. An apparatus of inspecting a substrate with a component mounted thereon, comprising:

an image capturer including a camera, the image capturer capturing an image reflected from a measurement object; and a central controller including at least one of the group including an image processing board, a control board, and an interface board, the central control unit extracting a shield region from the image and inspecting a defect of the component in an area excluding the shield region, wherein the shield region corresponds to such a region that at least a portion of a mounting state of the component is hid by a shield.

11. The apparatus of claim 10, wherein the central controller determines a region higher than a height of the component as the shield region.

12. The apparatus of claim 10, wherein the central controller applies an inspection condition, which is previously set, to the component under the shield region, after the shied region is recognized by using at least one of CAD information and component library information.

13. The apparatus of claim 10, wherein the image capturer captures a two-dimensional image, and the central controller determines the shield region using at least one of brightness and color of the two-dimensional image.

14. The apparatus of claim 10, wherein the central controller applies an inspection condition, which is previously set, to the component under the shied region, after recognizing the component under the shield region by using at least one of CAD information and component library information in order to inspect the component mounting failure in the area excluding the shield region.

15. The apparatus of claim 10, further comprising an illumination unit irradiating a pattern to the measurement object, wherein the image comprises a pattern image by the pattern, and wherein the central controller obtains a three-dimensional shape from the pattern image, and extracts the shield region from the three-dimensional shape.

* * * * *